United States Patent [19]

Marschner

[11] Patent Number: 4,664,909
[45] Date of Patent: * May 12, 1987

[54] STABLE SUSPENSION OF POWDER IN ALCOHOLIC MEDIA

[75] Inventor: Frank W. Marschner, Whitehouse Station, N.J.

[73] Assignee: Colgate-Palmolive Company, New York, N.Y.

[*] Notice: The portion of the term of this patent subsequent to Aug. 13, 2002 has been disclaimed.

[21] Appl. No.: 319,526

[22] Filed: Nov. 9, 1981

Related U.S. Application Data

[63] Continuation-in-part of Ser. No. 221,093, Dec. 29, 1980, abandoned.

[51] Int. Cl.⁴ .......................... A61K 7/32; A61K 7/36
[52] U.S. Cl. ............................ 424/65; 424/DIG. 5; 424/59; 424/67; 424/69
[58] Field of Search ............ 424/65, 361, 362, DIG. 5, 424/69

[56] References Cited

U.S. PATENT DOCUMENTS

| 74,871 | 2/1868 | Wilson | 424/65 |
| 279,195 | 6/1883 | Slocomb | 424/65 |
| 1,558,405 | 10/1925 | Smith | 424/65 |
| 2,145,583 | 1/1939 | Carlson | 424/65 X |
| 2,373,933 | 4/1945 | Weeks | 424/69 X |
| 2,602,042 | 7/1952 | Abbott | 424/65 |
| 3,152,181 | 10/1964 | Shapiro et al. | 424/65 X |
| 3,485,915 | 12/1969 | Serstein et al. | 424/65 X |
| 4,073,880 | 2/1978 | Pader et al. | 424/66 |
| 4,126,679 | 11/1978 | Davy et al. | 424/66 |

FOREIGN PATENT DOCUMENTS

| 968469 | 2/1952 | Fed. Rep. of Germany | 424/68 |
| 762847 | 4/1934 | France | 424/69 |
| 1187607 | 3/1959 | France | 424/69 |
| 1236071 | 6/1960 | France | 424/69 |
| 406561 | 12/1943 | Italy | 424/69 |
| 51-19114 | 2/1976 | Japan | 424/362 |
| 47804 | 4/1978 | Japan | 424/362 |
| 0040604 | 3/1980 | Japan | 424/362 |
| 26987 | of 1912 | United Kingdom | 424/362 |
| 908308 | 10/1962 | United Kingdom | 424/362 |

OTHER PUBLICATIONS

Pharmaceutical Formulas, 1947, vol. II, p. 152.
Martindale, The Extra Pharmacopocia, pp. 1705–1708, 1972.
American Perfumer & Cosmetics, 10/1963, vol. 78, pp. 95–97, Knectel.
Ash, A Formulary of Cosmetic Preparations, 1977, pp. 6, 11, 13, 14, 20, 24 and 25.

Primary Examiner—Dale R. Ore
Attorney, Agent, or Firm—Herbert S. Sylvester; Murray M. Grill; Norman Blumenkopf

[57] ABSTRACT

A novel fast drying stable pituitous powder suspension in an alcoholic/aqueous medium having a high alcohol content and a low water content, containing hydroxyethyl cellulose as the essential suspending agent, said alcohol content exceeding the upper solubility of hydroxyethyl cellulose in said alcohol and the water content being sufficient to prevent precipitation of said suspending agent and at least 5% by weight; having utility in the preparation of viscous liquid, semi-solid or solid suspension products such as creams or sticks, more specifically, roll-ons or stick deodorants and medicated lotions which may also be pump activated. The alcohol utilized herein is monohydric such as ethanol, methyl or isopropyl alcohol. However, a polyhydric alcohol such as propylene glycol, glycerine and/or polypropylene glycols may be partially substituted for the monohydric alcohol. Sodium or potassium bicarbonate suspensions have been found to be less irritating to the body and dry faster than bicarbonate solutions because the bicarbonate is delivered as a powder to be activated by body moisture.

14 Claims, No Drawings

STABLE SUSPENSION OF POWDER IN ALCOHOLIC MEDIA

This is a continuation-in-part of copending application Ser. No. 221,093, filed Dec. 29, 1980 now abandoned.

The present invention relates to stable pituitous suspensions of finely divided solids in aqueous/predominantly alcoholic media containing hydroxyethyl cellulose as the essential suspending agent, having particular utility in medicated lotions and personal care products such as roll-ons, pumps, lotions and on various substrates such as deodorant pads.

BACKGROUND AND PRIOR ART

Alcoholic based products are usually preferred for their fast drying and excellent solubilizing properties. However, inorganic salts are generally insoluble in alcohol so formulations require higher water to alcohol ratios which make wetter products that dry more slowly. Also salt concentrations are limited by their solubility in such systems. On the other hand the solubility of organic compounds (e.g. perfumes) depend on high alcohol content unless emulsified, so compromises are usually required. Certain salts such as sodium bicarbonate decompose in water or water/alcohol solutions and convert to sodium carbonate, so a powder suspension must be used.

Present novel aqueous alcoholic suspensions containing hydroxyethyl cellulose as the essential suspending agent allows alcohol soluble and insoluble ingredients to be used in fast drying products containing a high alcohol content.

The prior art is replete with compositions containing hydroxyethyl cellulose as a thickening agent per se or in combination with other thickening agents as disclosed in U.S. Pat. No. 4,002,881 which relates to a dentifrice, and in U.S. Pat. No. 4,145,413 which relates to a skin darkening composition. The hydroxyethyl cellulose forms an aqueous gel in aforesaid compositions, thereby effecting a thickening action.

Another group of compositions which utilize hydroxyethyl cellulose as a means of controlling drug release of a medicated tablet, are sustained release therapeutic formulations, as disclosed in U.S. Pat. Nos. 3,136,695, 4,235,870 and 4,167,558.

Hydroxyethyl cellulose has also been used as a stabilizer for a prostaglandin E group containing formulation as shown in U.S. Pat. No. 4,036,954; and as a film forming carrier for a medicament as shown in U.S. Pat. No. 4,136,162.

Stable aqueous dispersions or suspensions of solids or water insoluble compounds containing hydroxyethyl cellulose as one member of a stabilizing or suspending combination are disclosed in U.S. Pat. No. 3,258,326, which relates to a solid pesticidal agent in aqueous media; and by U.S. Pat. No. 3,927,205 which discloses an aqueous suspension of a water insoluble or sparingly soluble pharmaceutical. U.S. Pat. No. 3,287,222 additionally discloses an aqueous solution or suspension of a therapeutic agent containing hydroxyethyl cellulose as a thickening agent, useful as an impregnant for a synthetic medical dressing.

U.S. Pat. No. 3,290,218 further discloses that an aqueous or non-aqueous suspension of water-insoluble ethyl cellulose produces a stable suspension of a pharmaceutically or cosmetically active solid material. It is essential that said ethyl cellulose be substantially insoluble in the aqueous or non-aqueous carrier liquids.

Aqueous ethanol solutions of sodium or potassium bicarbonate as deodorant products have been disclosed in British Pat. No. 1,553,739. Although said bicarbonate solutions are efficacious deodorants, underarm irritation has been observed at the 10% level of potassium bicarbonate. It has also been found that aqueous or aqueous/alcoholic sodium bicarbonate solutions are pH unstable.

Aging studies have shown that the bicarbonate in solution breaks down liberating $CO_2$ and gradually converts into sodium carbonate (a known skin irritant). Bicarbonate solutions also have solubility limitations. Proportionately larger amounts of water are required for higher bicarbonate levels. Consequently less alcohol is permitted which results in wetter, slower drying products. Also, the preparation of sodium bicarbonate solutions above 6.9% are impossible due to its limited water solubility.

The prior art also discloses aerosol suspensions, dispensed via a pressurized container, containing sodium bicarbonate slurried with propellants in a 50:50 mixture in U.S. Pat. No. 2,959,225; and alkali metal bicarbonate in a 0.3 to 15% propellant-soluble vehicle such as ethanol with about 90% propellent in British Pat. No. 1,476,117. The difficulties and disadvantages encountered with aerosol suspensions of sodium or potassium bicarbonate discussed in aforesaid patents, include the settling and/or agglomeration of the dry particles, clogging of the dispensing nozzle, non-uniform spray of deodorant material, nonadherence of the bicarbonate deodorant to the sprayed area due to the bounce-off of said dry powder and/or too wet a spray resulting in too long a drying time, in addition to being detrimental to the environment.

Cosmetic sticks containing antiperspirants and/or sodium bicarbonate supended in a solid vehicle of a water-insoluble alcohol, such as cetyl alcohol and a silicone oil, is disclosed in U.S. Pat. No. 4,126,679. The difficulty of using sodium bicarbonate in this stick is due to its decomposition into sodium bicarbonate at relatively low temperatures as clearly shown in this patent.

However, there is no disclosure of a stable suspension of finely divided solids in an aqueous alcoholic media, such as ethanol, containing a high alcohol content and a minimal water content, by using hydroxyethyl cellulose as the essential suspending agent. The sodium or potassium bicarbonate pituitous suspension in said high alcoholic low water content media containing hydroxyethyl cellulose suspending agent substantially differs from the prior art aqueous or aqueous alcoholic solutions, aerosol suspensions and solid stick suspensions.

SUMMARY OF THE INVENTION

The primary object of the invention is to provide a stable, fast drying pituitous powder suspension in an alcoholic media containing a minimal amount of water and a critical amount of hydroxyethyl cellulose as the suspending agent.

Another object of the invention is to provide a stable fast drying pituitous suspension of particulate material in an aqueous alcoholic media containing hydroxyethyl cellulose at levels above its normal solubility limit in said alcoholic media.

Still another object of the invention is to provide stable, fast drying pituitous powder suspensions in alcohol which require little or no shaking prior to use.

Still another object of this invention is to provide a stable alcoholic/aqueous pituitous bicarbonate or other powder suspension containing hydroxyethyl cellulose as the essential suspending agent, which maintains said bicarbonate particles or other particulate material uniformly dispersed and suspended in said vehicle.

Another object of the invention is to provide a method of suspending powders in alcohol media by using hydroxyethyl cellulose at levels above its normal solubility limit, and a minimal amount of water, to obtain pituitous, pourable liquids in the preparation of liquid or solid alcoholic suspension products.

Additional objects, advantages and novel features of the invention will be set forth in part in the description which follows, and in part will become apparent to those skilled in the art upon examination of the following or may be learned by practice of the invention. The objects and advantages of the invention may be realized and retained by means of the instrumentalities and combinations particularly pointed out in the appended claims.

To achieve the foregoing and other objects and in accordance with the present invention, as embodied and broadly described herein, the product of this invention comprises a stable, fast drying, pituitous suspension of finely divided solids in a vehicle comprising at least about 50% lower aliphatic monohydric alcohol, at least about 5% and up to about 25% water, and hydroxyethyl cellulose as the essential suspending agent in an amount above its normal solubility.

More specifically, present invention relates to stable pituitous suspensions of particulate material, preferably about 1–20%, uniformly suspended in alcoholic/aqueous media containing a high alcohol content and a low water content. The alcoholic media may be a lower monohydric alcohol selected from the group consisting of methanol, ethanol, isopropanol and mixtures thereof. The use of polyhydric alcohols such as propylene glycol, butylene glycol and polyols thereof, and glycerin decreases the critical water level required in the hydroxyethyl cellulose-containing alcoholic media. The addition of alcohol soluble compounds such as oils, perfumes, etc. does not adversely affect the properties of present aqueous alcoholic powder suspensions. Similarly, the presence of co-suspending agents such as silica, bentonite and the like does not adversely affect the aqueous alcoholic powder suspension of present invention.

It has been unexpectedly found that powders can be suspended in alcoholic/aqueous media containing a high alcohol content and a low water content by using the water soluble polymer hydroxyethyl cellulose at critical levels above its ethanol solubility range which may be broadened by specified polyhydric alcohols. This polymer is unique in its property to form stable suspensions.

Although, hydroxyethyl cellulose is normally considered a thickener for aqueous type systems, it has been found to have unusual suspending properties in high alcohol/aqueous systems. Such suspensions are stringy and pituitous and offer superb suspending properties. This suspending agent gives exceptionally stable pituitous suspensions with no powder segregation after 13 weeks at 0, 40° F., ambient, 95° F., 110° F. and 120° F. temperature conditions, and require no shaking before use. This unexpected property of forming a stable pituitous powder suspension in a high alcohol/low water containing media is not possessed by other cellulosic derivatives such as hydroxypropyl cellulose, sodium carboxymethyl cellulose, hydroxypropylmethyl cellulose (Methocel) and other water soluble polymers. Utilizing 10% micropulverized sodium bicarbonate as the particulate material to be suspended in an alcoholic/aqueous media containing 25% water, the suspending properties of other water soluble cellulosic gums were tested by the addition of 0.4% hydroxypropyl methyl cellulose, 0.4% hydroxypropyl cellulose, or 0.8% sodium carboxymethyl cellulose. It was found that all the above samples separated with a clear water layer on top, the separation occurring within minutes. The physical appearance of the desired suspension is the formulation of a pituitous liquid which appears stringy when poured. Present novel alcoholic/aqueous hydroxyethyl cellulose-containing media provides outstanding suspending properties for powders, with excellent stability over wide temperature ranges. The products deliver well from roll-on and pump dispensers. The stringiness of the hydroxyethyl suspension system is believed to be responsible for its superior suspending properties.

In addition to the hydroxyethyl cellulose which is the essential suspending agent, it is optional to use co-suspending agents such as fumed silica (Cab-O-Sil) or bentonite in combination with the hydroxyethyl cellulose. The hydroxyethyl cellulose per se constitutes about 0.1–1% and the fumed silica or bentonite constitutes about 0.1–1%, and the total amount is preferably about 0.9–2% by weight of the total composition.

The particulate material suspended in the alcoholic/aqueous vehicle may be any inorganic or organic salt insoluble in alcohol such as sodium or potassium bicarbonate, zinc undecylenate, pigments, certain aluminum or zirconium compounds, and the like. More specifically, the suspended powder which is insoluble in alcohol may be selected from the group consisting of an inorganic or organic metal salt, pigment, mineral, polymer or salt thereof, or grain derived powders. It has been found that high levels of said salt or other powdered material, in excess of its water/alcohol solubility can be suspended in instant alcoholic/aqueous media containing hydroxyethylcellulose as suspending agent. The desirability of high levels of particulate material can hereby be formulated into stable alcoholic/aqueous media. It is preferable to use micropulverized powder, having a particle size of about 5 to 100 microns and preferably 10 to 25 microns. The smaller the particles, the easier it is to suspend in the vehicle, and the resultant product affords a non-gritty, smooth feel upon application and dryout on the skin. However, encapsulated powder either straight or in liquid or solid suspension may also be utilized. Although powder suspensions have essentially no concentration limitations and can be used at any efficacious level desired, amounts up to about 50% and as low as 1% may be suspended. stable pituitous suspensions of about 1–20% and preferably at least 5% sodium or potassium bicarbonate can be suspended in an alcoholic/aqueous media with essentially little or no bicarbonate in solution. This combination of high bicarbonate and high alcohol levels results in very effective fast drying non-irritating deodorant products. Said deodorant products evaporate rapidly leaving either a white (Baking Soda) residue or invisible film on the skin. The latter is achieved by adding non volatile polar or non-polar ingredients to the formula such as polyhydric alcohols or emollient oils.

It has been found that alcoholic/aqueous bicarbonate suspensions are highly desirable in aesthetics and superior to bicarbonate solutions. Bicarbonate solutions have been observed to cause skin irritation whereas bicarbonate suspensions are essentially non-irritating to the armpit. It has been discovered that aqueous or aqueous/alcoholic Sodium Bicarbonate solutions are pH unstable in aging studies. Bicarbonate in solution breaks down liberating $CO_2$ and gradually converts into sodium carbonate (a known skin irritant). Alcoholic-/aqueous bicarbonate suspensions on the other hand are pH stable thus explaining the non-irritating properties of this type product. It is also believed that Bicarbonate powder in suspension products can be control released by the addition of water insoluble ingredients which form a more water resistant film on dryout. This type of controlled release can further reduce the risk of skin irritation which cannot be achieved with aqueous/alcoholic bicarbonate solutions.

Skin irritation problems experienced with bicarbonate solutions can be explained as bicarbonate instability and its conversion into an irritating carbonate salt. Three products were made using 5% sodium bicarbonate as follows and examined for pH over a short aging period at 120° F.

|  | A<br>Water Soln. | B<br>Water<br>Alcohol Soln. | C<br>Alcohol/Water<br>Suspension |
| --- | --- | --- | --- |
| Distilled Water | 95.0 | 75.0 | 15.0 |
| Sodium Bicarbonate | 5.0 | 5.0 | 5.0 |
| SD 40 Ethanol | — | 15.0 | 79.6 |
| Hydroxyethyl Cellulose | — | — | 0.4 |
|  | 100.00 | 100.00 | 100.00 |
| pH (1:9 Parts Distilled Water) |  |  |  |
| Initial pH (After Making) | 8.6 | 8.7 | 8.62 |
| 4 days at 120° F. | 9.5 | 9.5 | 8.6 |
| 17 days at 120° F. | 9.9 | 9.9 | 8.6 | pH data shows the instability of both bicarbonate solutions and the superior stability of the suspension product. Bicarbonate in solution gradually releases $CO_2$ and converts into the higher alkaline irritating carbonate salt.

$$2NaHCO_3 \rightarrow Na_2CO_3 + H_2O + CO_2 \uparrow$$

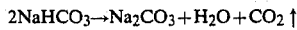

Formula (b) British Patent Specification No. 1,553,739 likewise showed pH instability at 120° F. and at ambient temperature.

| Natrosol 250 HR (hydroxyethyl cellulose) | 4.0 |
| --- | --- |
| Procetyl AWS (propoxylated cetyl alcohol) | 3.0 |
| Sodium Bicarbonate | 1.0 |
| Ethanol (SD 40) | 45.0 |
| Distilled Water | 47.0 |
|  | 100 |
| pH (1:10 Parts Distilled Water) |  |
| Initial pH (after making) | 8.8 |
| 124 hours later | — |
| Ambient Temperature | 9.4 |
| 120° F. | 9.95 |

Accordingly, an alcoholic/aqueous bicarbonate suspension deodorant offers many advantages and are unexpectedly superior to a bicarbonate solution deodorant product as evidenced by pH stability, non-irritating to the skin, fast drying properties, maximum deodorant protection and unlimited bicarbonate levels. Unlike bicarbonate solutions, bicarbonate in a suspension product is released by sweat secretion and the addition of water insoluble ingredients can further control and retard the release of bicarbonate under the armpit. In addition, a smooth, dry (talcum type) powder feel or smooth, non-gritty invisible film (with emollients) or white film (bicarbonate alone) is left on the skin.

The alcoholic/aqueous particulate suspensions of this invention require a suspending agent, otherwise said particles will settle and cake at the bottom of the container and cannot be adequately dispersed with shaking. Compounds used principally for thickening would slow down the settling rate, but offer no solution against compacting. Moreover, thickeners would in fact restrict the shaking motion for uniform particle redistribution. Suspending agents when used effectively prevent compacting of the particles and permit a uniform dispersion when shaken. The ideal suspension is one which requires essentially no shaking and where the particles remain uniformly suspended as exemplified in this invention.

The vehicle into which the particulate material is suspended comprises an alcoholic aqueous media, said alcohol being a monohydric alcohol which is a lower alkanol such as ethanol, isopropyl alcohol or methanol. Polyhydric alcohols can be partially substituted for the monohydric alcohol, not to exceed the monohydric alcohol content. Suitable polyhydric alcohols include glycerine, propylene glycol, butylene glycol and polyglycols thereof. The monohydric alcohol content, such as ethanol, must exceed the upper solubility level for the water soluble polymer hydroxyethyl cellulose in ethanol or other lower alkanol. The reported upper solubility level of this water soluble polymer in ethanol is 70%. Below this level and within normal soluble use ranges, a uniformly viscous liquid is obtained which pours evenly. Although, it appears aesthetically desirable, it will not support suspended powder and segregation occurs. However, at ethanol concentrations above its solubility range, the polymer becomes less soluble and forms the desired pituitous type liquid. If ethanol is further increased resulting in very low water levels the polymer will precipitate out and its suspending properties are again lost. Accordingly, a 70:30 ratio of ethanol-water is optimum. However, it was found that this problem can be eliminated by the sufficient addition of a polyhydric alcohol such as glycerine, propylene glycol, butylene glycol and polyglycols thereof. Accordingly, it has been found that the monohydric alcohol constitutes about 55-85%; and the water content may be as low as 5% if at least 10% polyhydric alcohol is also present in the suspension. The combined water and polyhydric alcohol content is at least about 15% and may be up to about 30% whereas the water content per se may be up to about 25%. Thus, it is apparent that the proportions of monohydric alcohol, water and polyhydric alcohol are interdependent.

Powder suspension products have essentially no concentration limitations and can be used at any efficacious level desired. However, suspensions do have water limitations and require higher alcohol to water ratios to provide stability to said stringy (pituitous) pourable liquid.

The pituitous aqueous alcoholic suspensions of this invention may be used in the intermediate preparation of alcohol based solid or semi-solid products, such as sticks or creams. It has been found particularly useful in the preparation of roll-on deodorants, deodorant sticks, medicated lotions, pump medicated rub and other fast-drying cosmetic formulations.

It has found particular application in the preparation of fast-drying, stable bicarbonate-containing deodorant products which require little or no shaking prior to use. These deodorant formulations utilizing suspensions of sodium or potassium bicarbonate have been found to be less irritating to the skin than bicarbonate solutions.

The deodorant product can also be formulated into a deodorant stick by the addition of a fatty acid salt, such as sodium stearate as a gelling agent. A sodium salt of a saturated higher fatty acid containing 14 to 22 carbon atoms ($C_{14}$–$C_{22}$), such as myristic, palmitic, stearic, etc. has been found effective as a gelling agent in the formation of a solid stick; whereas, the lower fatty acid salts and the unsaturated fatty acid salts do not function as gelling agents herein. The resultant stick is a solid pituitous suspension of deodorant active ingredient in an alcoholic/aqueous medium.

The intermediate use of the pituitous suspension prevents segregation after hot pouring into containers and permits a longer cooling down period for solidification. This is particularly advantageous, since in the conventional solidification of hot suspension compositions, rapid cooling which normally is about 1–5 minutes, is necessary in order to avoid segregation of suspended particles. Whereas, with present pituitous suspensions, the suspended particles do not separate or settle out, and longer periods of cooling is available, which is preferable in the formation of a solid stick.

The suspension deodorant products may also contain non-volatile polar or non-polar ingredients to effect the deposition of a dry, non-sticky invisible film on the skin upon evaporation, rather than a white bicarbonate residue. Said non-volatile agents include polyhydric alcohols such as glycerine, propylene glycol, butylene glycol and polyglycols thereof, and emollient oils, such as wheat germ oil, and any other alcohol soluble oils including isopropyl myristate, isopropyl palmitate, other fatty esters, fatty amides, fatty alcohols, fatty ethers such as stearyl ether, ethoxylated fatty alcohols and acids. The amount of emollient present is minor, about 1–5%. It has also been found that the presence of minor amounts of lipophylic agents such as oils, silicone, lecithin and waxes and/or water insoluble resins and polymers in this deodorant suspension product will control bicarbonate release under the armpit. It has been observed that the bicarbonate roll-on deodorant suspension containing the wheat germ oils and the stearyl ether oils form a water resistant film when dry which may explain the gradual release of bicarbonate under the armpit and reduce the risk of skin irritance. Test results have shown that most of the bicarbonate is released within 15 minutes with increasing amounts over 1 and 6½ hour periods showing time release characteristic of the dry film. Other deodorant agents may be substituted for the bicarbonate active ingredient.

In addition to the essential components of the present composition, one may also include therein minor amounts of components such as perfumes, coloring agents, ultraviolet absorbers to enhance the color, and the like, so as to improve the aesthetic value and consumer acceptability. Salts or pH buffering agents can be dissolved or suspended in instant alcoholic/aqueous suspension product if desired. Minor amounts of other ingredients which do not adversely affect the beneficial properties of instant composition may also be included.

Known bacteriostats may also be added. However, a bicarbonate suspension is effective as a deodorant without the use of added bacteriostats.

The suspensions of present invention have found utility in personal care deodorant products, such as roll-ons, pumps, on substrates such as deodorant pads, foot and body lotions.

Another application of present pituitous aqueous alcoholic media is in the preparation of fast-drying, stable medicated lotions containing a particulate active ingredient such as zinc undecylenate and other antifungal/antibacterial agent which may be dispensed via a pump or by simply spreading with the fingers. The same additives may be included in the medicated lotions as contained in the deodorant products.

The method of making the stable pituitous powder suspensions of instant invention generally comprises combining a heated aqueous or aqueous/monohydric or polyhydric alcohol mixture containing hydroxyethyl cellulose suspending agent with a monohydric alcoholic dispersion of a particulate material such as alkali metal bicarbonate or zinc undecylenate or the like which may contain a second suspending agent, and mixing until a thick stable pituitous, stringy suspension is formed. More specifically, a clear Part 1 viscous solution of hydroxyethyl cellulose is prepared by heating and mixing with water or a water containing mixture of monohydric or polyhydric alcohol to a temperature of about 130°–140° F. A Part 2 preferably homogenized dispersion of particulate material in a monohydric alcohol with or without a suspending agent is added with mixing to Part 1 viscous mixture to form a thick uniform pituitous, stringy suspension wherein the solid particles are uniformly suspending and remain in suspension. The perfume, colorants, emollients and other optional ingredients may be added to the alcoholic particulate dispersion prior to its addition to the aqueous/alcoholic viscous hydroxyethyl cellulose solution, or subsequent thereto. The final suspension as well as each of the two dispersions independently, is preferably homogenized to effect a homogeneous final thick, pituitous suspension product. If a stick is desired, a suitable gelling agent such as a sodium salt of a saturated $C_{14}$–$C_{22}$ fatty acid (i.e., myristic, palmitic, stearic, etc. fatty acid) is dissolved in Part 1, and the final pituitous suspension is poured into stick containers and allowed to coolant room temperature. The final product is a solid pituitous suspension of powder in an alcoholic/aqueous media containing hydroxyethyl cellulose.

Another method of making the stable pituitous particulate suspensions comprises the sequential addition of the ingredients to a heated solution (about 140° F.) of water and alcohol, with agitation and/or homogenization. More specifically, the hydroxyethyl cellulose is added to the warm aqueous/alcoholic solution, followed by the monohydric alcohol followed by another suspending agent if desired, followed by the particulate material, followed by the perfume, color and any other optional ingredient. This method yields a thinner suspension than when utilizing the aforementioned two part method. Either method however requires the initial preparation of a viscous aqueous containing hydroxyethyl cellulose solution prior to the addition of final amounts of monohydric alcohol. Accordingly, the order of addition and the preparation methods are important in achieving the desired pituitous suspension.

DETAILED DESCRIPTION OF THE INVENTION

The following specific examples are further illustrative of the present invention, but it is understood that the invention is not limited thereto. All amounts of various ingredients are by weight unless otherwise specified.

EXAMPLES 1-4

|  | 1 | 2 | 3 | 4 |
|---|---|---|---|---|
| Part 1 | | | | |
| Deionized Water | 15.00 | 15.00 | 5.00 | 15.00 |
| Propylene Glycol | — | 10.00 | 10.00 | — |
| SD 40 Ethanol | 10.00 | — | — | 15.00 |
| Natrosol 250 HR[1] | 0.40 | 0.40 | 0.40 | 0.40 |
| Part 2 | | | | |
| SD 40 Ethanol | 63.15 | 60.65 | 70.65 | 56.10 |
| Cab-O-Sil[2] | 0.50 | 0.50 | 0.50 | 0.50 |
| Sodium Bicarbonate (Micropulverized) | 10.00 | 10.00 | 10.00 | 5.00 |
| Zinc Ricinoleate | — | — | — | 5.00 |
| Part 3 | | | | |
| Perfume | 0.50 | 0.50 | 0.50 | 0.50 |
| FD & C Green No. 3 (.1%) | 0.30 | 0.30 | 0.30 | — |
| D & C Green No. 8 (2.75%) | 0.10 | 0.15 | 0.15 | — |
| Arlamol E[3] | — | 1.50 | 1.50 | 1.50 |
| Wickenol 535[4] | — | 1.00 | 1.00 | 1.00 |
|  | 100.00 | 100.00 | 100.00 | 100.00 |
| pH 1% aqueous Solution | 8.45 | — | — | — |
| Appearance | Thick, viscous pituitous suspension | Thick, viscous pituitous suspension | Thick, viscous pituitous suspension | Lotion consistency pituitous suspension |

Example 1 drys rapidly to a smooth dry non-sticky white powder on the skin.
Examples 2, 3, 4 dry to a smooth dry non-sticky invisible film on the skin.
[1]Natrosol 250 HR: Hercules Inc., Hydroxyethyl Cellulose
[2]Cab-O-Sil: Cabot Corporation, Fumed Silica
[3]Arlamol E: I.C.I. American Inc., Polyoxypropylene Stearyl Ether
[4]Wickenol 535: Wickhen Products Inc., Wheat Germ Glycerides All examples show no bicarbonate or liquid separation on standing and require no shaking before use, and are non-irritating to the skin.

Aging tests over a period of two weeks at room temperature, 40° F. and 110° F. show no bicarbonate segregation.

Preparation of Examples

Step 1
Part 1 (all examples): Disperse Natrosol in either Ethanol or Propylene Glycol. Add water with constant mixing and heat to 130°-140° F. until a uniform clear viscous solution is formed.

Step 2
Part 2 (Examples 1-3): Disperse Cab-O-Sil in alcohol and add Sodium Bicarbonate gradually with rapid mixing. Homogenize until uniform.

(Example 4): Dissolve Zinc Ricinoleate in warm Ethanol. Add Sodium Bicarbonate and Cab-O-Sil and mix. Homogenize until uniform.

Step 3
Add Part 2 to Part 1 with mixing (thick pituitous stringy suspension is formed).

Step 4
Part 3: Admix all ingredients with Parts 1 and 2. Homogenize mixture into a thick uniform pituitous suspension.

EXAMPLE 5

| Ingredient | % |
|---|---|
| Propylene Glycol | 10.0 |
| Bentone LT[1] | 0.5 |
| Deionized Water | 15.0 |
| Sodium Bicarbonate Micropulverized | 10.0 |
| SD 40 Ethanol | 64.5 |
|  | 100.0 |

[1]Bentone LT: NL Industries Gellant is an organoclay material product designed for low molecular weight polar solvent/water systems and 100% water systems. It is a combination of hydroxyethyl cellulose and bentonite clay.

This example also forms a good uniform pituitous suspension since Bentone LT is a combination of hydroxyethyl cellulose and bentonite clay. This example shows the specificity of this specific suspending agent in the formation of a stable pituitous viscous suspension in accordance with the present invention.

Preparation of Example 5

1. Disperse Bentone LT in Propylene Glycol.
2. Add water, and heat to 130°-140° F. until uniformly viscous.
3. Add Sodium bicarbonate - mix continuously.
4. Add alcohol, mix completely until uniform and homogenize.

EXAMPLE 6

Example 2 is repeated except that the stearyl ether and wheat germ glycerides are omitted and the ethanol content is increased to 63.15%. This product yields a stable uniform pituitous suspension of high viscosity from which the bicarbonate particles do not separate out upon standing but remain in suspension. This product, used in a roll-on container with a one-inch ball, gives good delivery and fast drying properties to form an invisible film on the skin.

EXAMPLES 7 and 8

|  | 7 Roll-on Deodorant | 8 Pump Medicated Rub |
|---|---|---|
| Part 1 | | |
| Water | 15.00 | 17.0 |
| Propylene Glycol | 10.00 | 10.00 |
| Natrosol 250 HR[1] | 0.40 | 0.4 |
| Part 2 | | |
| SD 40 Ethanol | 60.40 | 64.3 |
| Cab-O-Sil[2] | 0.50 | 0.5 |
| Sodium Bicarbonate (Micropulverized) | 10.0 | — |
| Zinc Undecylenate | — | 5.0 |
| Part 3 | | |
| Wheat Germ Glycerides | 1.00 | 1.0 |
| Arlamol E[3] | 1.50 | 1.5 |
| Perfume | 0.50 | 0.3 |
| Color Solution | 0.65 | — |
| Uvinul D-50[5] | 0.05 | — |
|  | 100.00 | 100.00 |

[5]Ultraviolet absorber 2,4-dihydroxybenzophenone: GAF corporation.

Procedure

Part 1: Combine water and Propylene Glycol and add Natrosol gradually with mixing. Heat to 140° F. to form a uniform viscous mixture.

Part 2: Homogenize Cab-O-Sil then Sodium Bicarbonate or Zinc Undecylenate in Ethanol. Add Part 2 gradually to Part 1 with mixing.

Part 3: Add mix part 3 ingredients to parts 1 and 2, then homogenize complete mixture.

Results

Both products form a stringy pituitous white opaque liquid with excellent suspending properties. No significant Sodium bicarbonate segregation is observed in Example 7 after 13 weeks aging over a wide temperature range.

EXAMPLE 7

Stability at various Temperature (unshaken)

| Temperature Conditions | 0 | 40° F. | Ambient | 95 F. | 110 F. | 120 F. |
|---|---|---|---|---|---|---|
| % NaHCO$_3$ Analyzed (Top ¼" of liquid) | 10.6 | 10.5 | 10.6 | 10.6 | 10.3 | 10.1 |

Ambient temperature Shaken Control = 10.7

The following examples illustrate the effect of water levels on the formation and stability of the desired suspensions and the advantage of adding a polyhydric alcohol to low moisture formulations.

EXAMPLES 9–14

| Example | 9 | 10 | 11 | 12 | 13 | 14 |
|---|---|---|---|---|---|---|
|  | % | % | % | % | % | % |
| Part 1 | | | | | | |
| Water | 37.7 | 25.0 | 15.0 | 15.0 | 5.0 | 15.0 |
| Propylene Glycol | 10.0 | — | — | 10.0 | 20.0 | — |
| Glycerine | — | — | — | — | — | 10.0 |
| Natrosol | 0.4 | 0.4 | 0.4 | 0.4 | 0.4 | 0.4 |
| Part 2 | | | | | | |
| SD 40 Ethanol | 37.7 | 64.4 | 74.6 | 64.6 | 60.4 | 64.6 |
| Cab-O-Sil | 0.5 | — | — | — | 0.5 | — |
| Sodium Bicarbonate (Micropulverized) | 10.0 | 10.0 | 10.0 | 10.0 | 10.0 | 10.0 |
| Part 3 | | | | | | |
| Consists of oils, perfume | 3.7 | — | — | — | 3.7 | — |
| Color, UV absorber | — | 0.2 | — | — | — | — |
|  | 100.0 | 100.0 | 100.0 | 100.0 | 100.0 | 100.0 |
| Appearance: | uniformly viscous | pituitous | not homogeneous | pituitous | pituitous | pituitous |
| Stability: | Separated on standing | Stable | Separation | Stable | Stable | Stable |
| Remarks: | excess water | water level about right | insufficient water | Satis. Propylene Glycol Compensation | Satis. Propylene Glycol Compensation | Satis. Glycerine Substitution |

Procedure:

Similar procedure is used as in Examples 7 and 8 except for formula 13. Half the formula amount of propylene Glycol is combined with water, Natrosol is added, and the mixture is heated to 140° F. with mixing until uniformly thick. The balance of Propylene Glycol is added and mixed prior to adding part 2.

Stability after 5 Weeks (Ambient Temperature—unshaken)

| Examples | 10 | 12 | 13 | 14 |
|---|---|---|---|---|
| % NaHCO$_3$ Analyzed (Top ¼" of liquid) | 10.3 | 10.6 | 10.5 | 10.1 |

EXAMPLE 15

Medicated Rubbing Lotion

|  | % |
|---|---|
| Part 1 | |
| Deionized Water | 24.0 |
| Hydroxyethyl cellulose | 0.4 |
| Isopropanol | 15.0 |
| Part 2 | |
| Isopropanol | 53.1 |
| Cab-O-Sil | 0.5 |
| Zinc Undecylenate | 5.0 |
| Perfume | 0.5 |
| Zinc Stearate | 1.5 |

Procedure:

Part 1: Disperse the hydroxyethyl cellulose in alcohol, add water and heat the mixture with mixing to 140° F.

Part 2: Add Cab-O-Sil to alcohol and mix well. Add Zinc undecylenate and mix this dispersion well. Add zinc stearate and perfume and mix. Mix Parts 1 and 2. A thick pituitous gel is formed of cream consistency.

Upon application to the skin, it exhibits a very smooth after feel and is reasonably water repellant under water.

EXAMPLE 16

Example 8 is repeated except that the water content is decreased to 14% and the ethanol content is increased to 67.3%. The resultant product is a good suspension having a stringy consistency.

EXAMPLE 17

Deodorant Stick

|  | % |
|---|---|
| Part 1 | |
| Deionized Water | 5.0 |
| Propylene glycol (Part 1) | 10.0 |
| Hydroxyethyl cellulose | 0.4 |
| Propylene glycol (Part 2) | 15.0 |
| Sodium stearate | 6.0 |
| Part 2 | |
| Anhydrous ethanol | 53.1 |
| Cab-O-Sil | 0.5 |
| Micropulverized NaHCO$_3$ | 10.0 |

Part 1: Mix the water and Part 1 propylene glycol and add the hydroxyethyl cellulose. Heat the mixture to 140°–150° F. until the viscous gel is formed. Part 2 propylene glycol is added and mixed well to form a homogeneous thick gel solution. Sodium stearate is added and the mixture is heated to 150°–160° F. until the sodium stearate is completely dissolved.

Part 2: The Cab-O-Sil is dispersed in the ethanol and the sodium bicarbonate is added and mixed until uniformly dispersed and suspended. The mixture is heated to about 135° F.

Part 2 is added to Part 1 with mixing to form a viscous pituitous suspension which is poured into stick containers and allowed to cool at room temperature. No apparent segregation occurs. An excellent suspension in stick form is obtained, which is slick upon application and non-sticky.

Other polyhydric alcohols can be substituted for the propylene glycol or glycerine in part or in total in the above examples, such as butylene glycol, polypropylene glycol, etc. Similarly the ethanol and the isopropanol can be replaced by methanol. Likewise, other particulate material can be substituted for the sodium bicarbonate and zinc undecylenate such as potassium bicarbonate, inorganic or organic salts or other alcohol insoluble powders.

All of the alcoholic/aqueous pituitous suspensions containing a particulate active ingredient have been found to be highly effective cosmetic products, are stable, non-irritating, faster drying and the active ingredient is delivered as a powder to be activated by the body moisture at the area of contact.

Although the present invention has been described and illustrated with reference to specific examples, it is understood that modifications and variations of composition and procedure are contemplated within the scope of the following claims.

I claim:

1. A fast drying, stable pituitous powder suspension of alcohol insoluble finely divided solid particles uniformly suspended in a vehicle comprising a high alcohol content of lower aliphatic monohydric alcohol and a low water content and hydroxyethyl cellulose suspending agent, said monohydric alcohol content exceeding the upper solubility level for the water soluble hydroxyethyl cellulose in said alcohol and within the range of about 55-85%, and the water content being sufficient to prevent precipitation of said suspending agent and at least 5% if at least 10% polyhydric alcohol is also present in the suspension, and up to about 25% by weight.

2. The composition in accordance with claim 1, wherein an alkali metal salt of a saturated $C_{14}$-$C_{22}$ fatty acid gelling agent is added to the pituitous suspension to form a solid suspension.

3. The composition in accordance with claim 2, wherein the solid suspension is a deodorant stick.

4. The composition in accordance with claim 1, wherein the suspension is in the form of a viscous lotion.

5. The composition in accordance with claim 4, wherein the suspension is a medicated lotion.

6. The composition in accordance with claim 5, wherein the suspended powder is zinc undecylenate.

7. The composition in accordance with claim 1, containing a polyhydric alcohol in an amount not to exceed the monohydric alcohol content and sufficient to prevent precipitation of the suspending agent.

8. The composition of claim 7, wherein the polyhydric alcohol is selected from the group consisting of glycerine, propylene glycol, butylene glycol and polyglycols thereof.

9. The composition of claim 1, wherein the monohydric alcohol is selected from the group consisting of ethanol, methanol and isopropyl alcohol.

10. The composition of claim 1, also containing nonvolatile polar or non-polar ingredients selected from the group consisting of polyhydric alcohols and emollient oils.

11. A method of making the suspension of claim 1 which comprises the initial preparation of viscous aqueous-containing hydroxyethyl cellulose solution prior to the addition of the monohydric alcohol and the powdered material.

12. The method of making the pituitous suspension of claim 1, which comprises preparing a clear viscous aqueous or aqueous alcoholic solution of hydroxyethyl cellulose heated to a temperature of about 130°-140° F., mixing this heated viscous solution with a monohydric alcoholic dispersion of the powdered material until a viscous pituitous suspension is formed with the powdered particles uniformly suspended therein.

13. The method of claim 12, wherein a sodium salt of a saturated $C_{14}$-$C_{22}$ fatty acid gelling agent is dissolved in the heated hydroxyethyl cellulose solution prior to mixing with the alcoholic dispersion of the powdered material, pouring the pituitous suspension into stick containers and allowing to cool at room temperature.

14. The composition in accordance with claim 1, wherein the suspended powder is insoluble in alcohol and selected from the group consisting of inorganic or organic metal salts, pigments, minerals, polymers or salts thereof or grain derived powders.

* * * * *